US010562858B2

(12) United States Patent
Sasaki et al.

(10) Patent No.: US 10,562,858 B2
(45) Date of Patent: Feb. 18, 2020

(54) CRYSTALLINE ANTI-TRICHOPHYTON AGENTS AND PREPARATION PROCESS THEREOF

(71) Applicant: MEIJI SEIKA PHARMA CO., LTD., Chuo-ku, Tokyo (JP)

(72) Inventors: Toshiro Sasaki, Odawara (JP); Takahiro Imai, Odawara (JP); Kenichiro Mori, Odawara (JP); Makoto Ohyama, Yokohama (JP); Takashi Watanabe, Yokohama (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/503,094

(22) PCT Filed: Aug. 12, 2015

(86) PCT No.: PCT/JP2015/072817
§ 371 (c)(1),
(2) Date: Feb. 10, 2017

(87) PCT Pub. No.: WO2016/024602
PCT Pub. Date: Feb. 18, 2016

(65) Prior Publication Data
US 2017/0233346 A1    Aug. 17, 2017

(30) Foreign Application Priority Data
Aug. 13, 2014 (JP) .................. 2014-165038

(51) Int. Cl.
*C07D 231/12* (2006.01)
*C07F 5/02* (2006.01)
*C07D 231/10* (2006.01)

(52) U.S. Cl.
CPC ........ *C07D 231/10* (2013.01); *C07D 231/12* (2013.01); *C07F 5/02* (2013.01); *C07F 5/025* (2013.01)

(58) Field of Classification Search
CPC ........... C07D 231/12; C07F 5/02; C07F 5/025
See application file for complete search history.

(56) References Cited

U.S. PATENT DOCUMENTS

| | | | |
|---|---|---|---|
| 4,475,944 A | 10/1984 | Rorer | |
| 4,826,867 A | 5/1989 | Jensen-Korte et al. | |
| 6,727,401 B1 | 4/2004 | Venkateshwaran et al. | |
| 6,916,814 B2 | 7/2005 | Moss et al. | |
| 7,265,224 B2 | 9/2007 | Park et al. | |
| 8,771,726 B2 | 7/2014 | Toshimitsu et al. | |
| 8,889,727 B2 * | 11/2014 | Ohyama | C07D 231/12 514/406 |
| 10,123,978 B2 * | 11/2018 | Kawahara | A61K 9/7061 |
| 2004/0152725 A1 | 8/2004 | Moss et al. | |
| 2006/0193900 A1 | 8/2006 | Yasukochi et al. | |
| 2010/0282269 A1 | 11/2010 | Uchida et al. | |
| 2010/0291012 A1 | 11/2010 | Guy et al. | |
| 2013/0317074 A1 | 11/2013 | Ohyama et al. | |
| 2014/0030209 A1 | 1/2014 | Furuta et al. | |

FOREIGN PATENT DOCUMENTS

| | | | |
|---|---|---|---|
| CA | 2825889 A1 * | 8/2012 | ........... C07D 231/12 |
| EP | 2669274 A1 | 12/2013 | |
| ES | 2015648 A6 | 9/1990 | |
| JP | 63068569 A | 3/1988 | |
| JP | 2003344278 A | 12/2003 | |
| JP | 2005118398 A | 5/2005 | |
| JP | 2008169155 A | 7/2008 | |
| JP | 4284169 B2 | 6/2009 | |
| JP | 2010189440 A | 9/2010 | |
| JP | 2011140504 A | 7/2011 | |
| JP | 2012036198 A | 2/2012 | |
| WO | 9503775 A1 | 2/1995 | |
| WO | 03005999 A2 | 1/2003 | |
| WO | 2004033432 A1 | 4/2004 | |
| WO | 2004084826 A2 | 10/2004 | |
| WO | 2008024978 A2 | 2/2008 | |
| WO | 2012102404 A1 | 8/2012 | |

OTHER PUBLICATIONS

International Search Report (ISR) and Written Opinion dated Sep. 29, 2015 issued in International Application No. PCT/JP2015/072817.
Stephen Byrn, et al., "Pharmaceutical Solids: A Strategic Approach to Regulatory Considerations", Pharmaceutical Research, vol. 12, No. 7, 1995, pp. 945-954.
Mik Bavin, "Polymorphism in Process Development", Chemistry & Industry, Aug. 21, 1989, pp. 527-529.
Yusaka Shioji, "Kokei Seizai no Seizo Gijutsu", CMC Publishing Co., Ltd., Jan. 27, 2003, p. 12, No English translation provided.
Shozo Asahara, et al., Yozai Handbook, Kodansha Ltd., Sep. 1, 1985, pp. 47-51, No English translation provided.
RN 83430-98-2, Database Registry Chemical Abstracts Service, Columbus, Ohio, Accession No. RN 83430-98-2, Entered STN: Nov. 16, 1984.
A. K. Gupta, et al., "Prevalence and epidemiology of toenail onychomycosis in diabetic subjects: a multicentre survey", British Journal of Dermatology 1998, 139, pp. 665-671.
BASF, "Kollidon VA64 Fine", Aug. 2011 (abstract).
K. Anandarajagopal, et al., "Antiepileptic and Antimicrobial Activities of Novel 1-(unsubstituted/substituted)-3,5-dimethyl-1H-pyrazole Derivatives", International Journal of ChemTech Research, vol. 2, No. 1, pp. 45-49, Jan.-Mar. 2010.

(Continued)

*Primary Examiner* — Laura L Stockton
(74) *Attorney, Agent, or Firm* — Holtz, Holtz & Volek PC

(57) ABSTRACT

A crystal form of 2-(3,5-dimethyl-1H-pyrazol-1-yl)-5-methylphenol which is stable and has high purity for preservation, industrial manufacturing, and circulation, and process for providing the same by using a boron compound.

15 Claims, 1 Drawing Sheet

(56) References Cited

OTHER PUBLICATIONS

Kenzo Sirakawa, et al., "[Pyrazolyl1-(1)-pyrimidine", Annual Report of Takeda Research Center, 1963, vol. 22, pp. 27-46.
Fukata, "Cyclodienones. 9. Reaction of 4-Halo-2, 4, 6-Tri-Tert-Butyl-2, 5-Cyclohexadien-1-Ones With Pyrazoles and Preparation of 1-(2-Hydroxyphenyl) and 1-(4Hydroxyphenyl) Pyrazoles", Heterocycles, 1982, vol. 19, No. 8, pp. 1478-1495.
Ito, et al., "A medium-term rat liver bioassay for rapid in vivo detection of carcinogenic potential of chemicals", Cancer Science, 94(1), 3-8 (2003).
Schneider, et al., "Skin Cosmetics", Ullmann's Encyclopedia of Industrial Chemistry; Jan. 15, 2001; Wiley-VCH Verlag GmbH & Co. KGaA.
Yamaguchi, "Pathogenic Fungi and Mycosis", Nanzando Co., Ltd., Revised 2nd Edition, 2003, pp. 184-187.
Yamaguchi, "Pathogenic Fungi and Mycosis", Nanzando Co., Ltd., Revised 2nd Edition, 2003, pp. 42-45.

\* cited by examiner

CRYSTALLINE ANTI-TRICHOPHYTON AGENTS AND PREPARATION PROCESS THEREOF

TECHNICAL FIELD

The present invention relates to a novel preparation process of 2-(3,5-dimethyl-1H-pyrazol-1-yl)-5-methylphenol useful as an anti-trichophytin agent, and its crystals.

BACKGROUND ART

It has been reported that 2-(3,5-dimethyl-1H-pyrazol-yl)-5-methylphenol is useful as an anti-trichophyton agent (Patent Document 1).

In Patent Document 1, as preparation processes of 2-(3,5-dimethyl-1H-pyrazol-1-yl)-5-methylphenol represented by the formula (1), the following two processes are disclosed.

Scheme 1

[Formula 1]

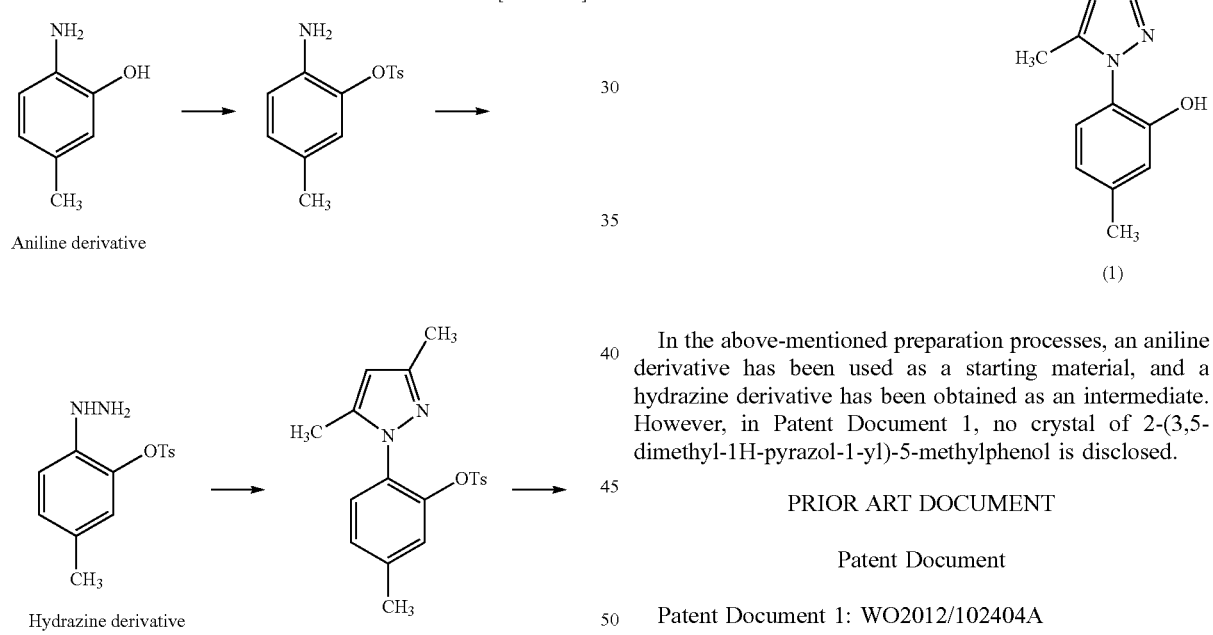

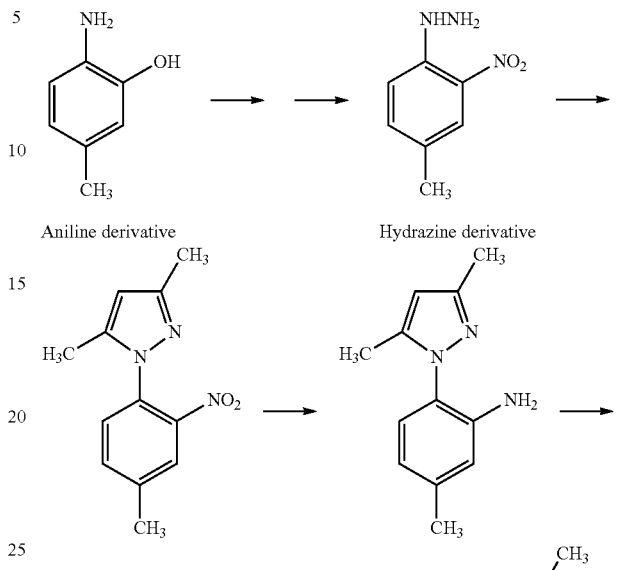

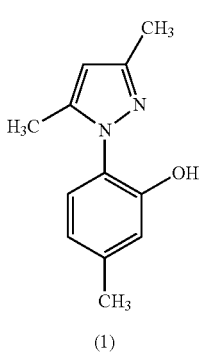

(1)

In the above-mentioned preparation processes, an aniline derivative has been used as a starting material, and a hydrazine derivative has been obtained as an intermediate. However, in Patent Document 1, no crystal of 2-(3,5-dimethyl-1H-pyrazol-1-yl)-5-methylphenol is disclosed.

PRIOR ART DOCUMENT

Patent Document

Patent Document 1: WO2012/102404A

SUMMARY OF THE INVENTION

Problems to be Solved by the Invention

An active pharmaceutical ingredient can have substantially different physical characteristics depending on the difference in its solid form. Such difference in physical characteristics can have an influence, for example, on easiness of handling, easiness of processability, storage stability, etc., of an active pharmaceutical ingredient. Accordingly, it has been desired to establish an industrial preparation process of crystalline active pharmaceutical ingredients which can be stably preserved and easily handled. It has also been desired to establish a preparation process which is reduced in an exposure amount of a harmful ingredient(s) and has higher safety for industrialization.

In Patent Document 1, 2-(3,5-dimethyl-1H-pyrazol-1-yl)-5-methylphenol can be obtained in an oily state, and it can be also obtained as a solid by freeze-drying the oil using dioxane as a solvent. However, according to the preparation process of Patent Document 1, the compound could not be obtained as crystals.

Also, since the compound is used as a medicine, in the preparation process thereof, it has been desired to use a process using starting materials and intermediates having higher safety without using an aniline derivative or a hydrazine derivative.

Means to Solve the Problems

The present inventors have intensively studied to solve the above-mentioned problems, and as a result, we have found a preparation process of 2-(3,5-dimethyl-1H-pyrazol-1-yl)-5-methylphenol having higher safety than the conventional processes and crystals of 2-(3,5-dimethyl-1H-pyrazol-1-yl)-5-methylphenol.

That is, the present invention relates to:

[1] crystals of a compound represented by the following formula (1):

[Formula 3]

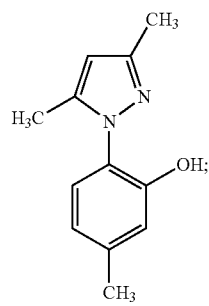

(1)

[2] the crystals described in [1], wherein the crystals show characteristic peaks at diffraction angles (2θ±0.2) of 9.3°, 16.6°, 19.2°, 21.6° and 21.9° in a powder X-ray diffraction pattern;

[3] the crystals described in [1], wherein the crystals show characteristic peaks at diffraction angles (2θ±0.2) of 9.3°, 12.7°, 16.6°, 17.3°, 17.9°, 19.2°, 21.3°, 21.6°, 21.9° and 25.7° in a powder X-ray diffraction pattern;

[4] the crystals described in [1], wherein the crystals show characteristic peaks at diffraction angles (2θ±0.2) of 93°, 12.7°, 16.6°, 17.3°, 17.9°, 19.2°, 21.3°, 21.6°, 21.9°, 24.0° and 25.7° in a powder X-ray diffraction pattern;

[5] a process for preparing a compound represented by the following formula (1):

[Formula 6]

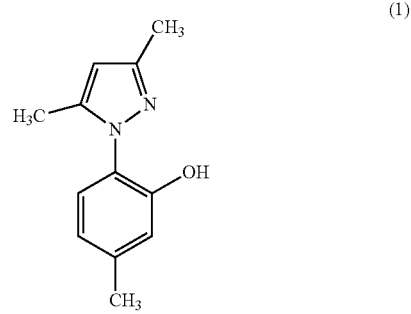

(1)

which comprises the step of reacting a compound represented by the following formula (2):

[Formula 4]

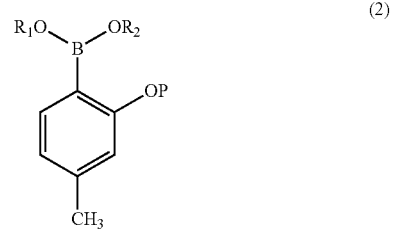

(2)

wherein $R_1$ and $R_2$ each independently represent a hydrogen or a $C_{1-6}$ alkyl, or $R_1$ and $R_2$ are combined together to form a linear or branched $C_{2-6}$ alkylene, and P represents a hydrogen atom or a protective group for a hydroxy group, with a compound represented by the following formula (3):

[Formula 5]

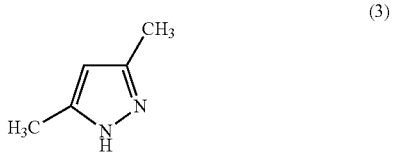

(3)

in the presence or absence of a base, and when P represents a protective group for a hydroxy group, which comprises the step of removing the protective group P;

[6] the process described in [5], wherein the reaction of the compound represented by the formula (2) with the compound represented by the formula (3) is carried out by using a copper reagent as a catalyst;

[7] the process described in [5] or [6], wherein $R_1$ and $R_2$ of the compound represented by the formula (2) are combined together to form a 2,3-dimethylbutan-2,3-diyl group;

[8] the process described in any one of [5] to [7], wherein the reaction of the compound represented by the formula (2) with the compound represented by the formula (3) is carried out in the absence of a base;

[9] a process for preparing a compound represented by the following formula (1):

[Formula 9]

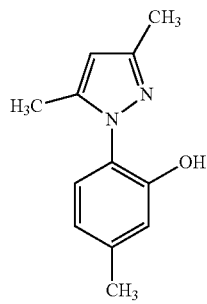
(1)

which comprises the steps of reacting a compound represented by the following formula (5):

[Formula 7]

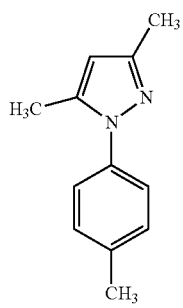
(5)

with an alkyl lithium reagent and a boric acid ester to obtain a compound represented by the formula (6):

[Formula 8]

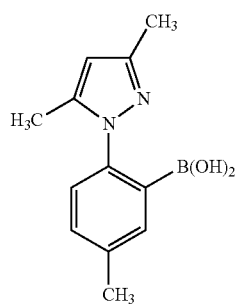
(6)

and further oxidizing the resulting compound represented by the formula (6);

[10] a compound represented by the following formula (6):

[Formula 10]

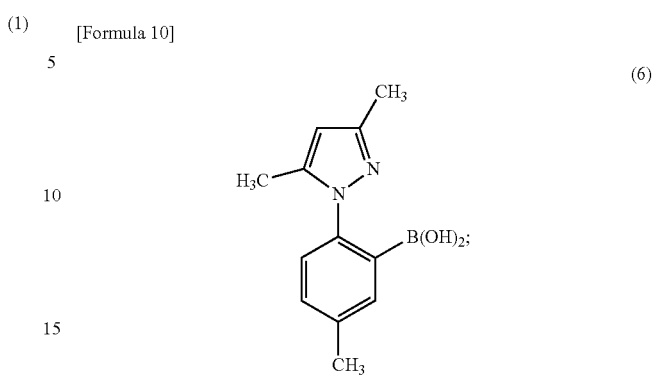
(6)

[11] a pharmaceutical composition comprising the crystals described in any one of [1] to [4];
[12] an anti-trichophyton agent comprising the crystals described in any one of [1] to [4].

Effects of the Invention

According to the present invention, a preparation process of 2-(3,5-dimethyl-1H-pyrazol-1-yl)-5-methylphenol useful as an anti-trichophyton agent having high safety can be provided by avoiding use of an aniline derivative and a hydrazine derivative. Further, crystals of 2-(3,5-dimethyl-1H-pyrazol-1-yl)-5-methylphenol useful as an active pharmaceutical ingredient can be unexpectedly obtained.

The crystals obtained by the present invention have extremely high stability, so that preservation or handling thereof is easy and simple without setting specific preservation conditions, so that it is possible to provide crystals extremely advantageous for industrial manufacturing in terms of formulation, circulation, etc.

EMBODIMENTS TO CARRY OUT THE INVENTION

Figure 1:
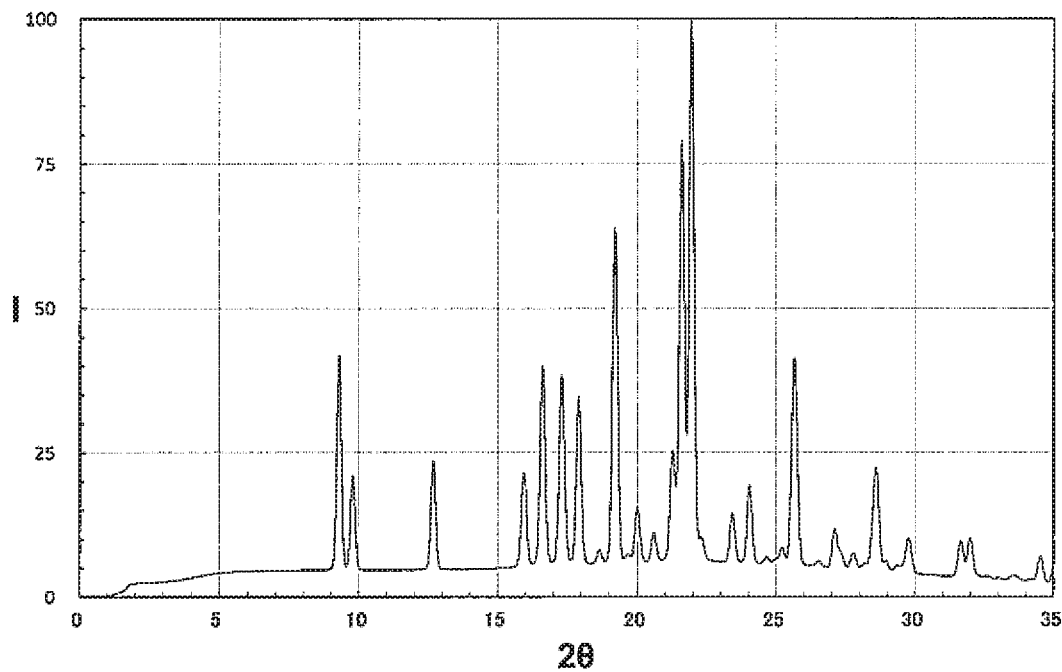
FIG. 1 is a drawing showing a powder X-ray diffraction pattern of Form A of the formula (1).

In the following, the contents of the present invention are explained in detail.

Here, the term "$C_{1-6}$ alkyl" used in the present specification represents a monovalent hydrocarbon group which may be a linear, branched or cyclic and having 1 to 6 carbon atoms. There may be mentioned, for example, a $C_{3-6}$ cycloalkyl group such as cyclopropyl, cyclobutyl, cyclopentyl, cyclohexyl, etc., in addition to methyl, ethyl, propyl, isopropyl, butyl, isobutyl, sec-butyl, tert-butyl, pentyl, hexyl, etc. It is preferably mentioned methyl, ethyl, propyl, isopropyl, butyl, isobutyl, tert-butyl, more preferably isopropyl.

In addition, "$C_{2-6}$ alkylene" represents a linear or branched divalent hydrocarbon group having 2 to 6 carbon atoms. There may be mentioned, for example, ethylene, propylene, isopropylene, butylene, isobutylene, sec-butylene, tert-butylene, 2,3-dimethylbutan-2,3-diyl, pentylene, hexylene, etc. It is preferably mentioned 2,3-dimethylbutan-2,3-diyl.

According to one embodiment of the present invention, the compound of the formula (1) can be prepared with good efficiency by the process according to the following Scheme, and further the compound of the formula (1) can be obtained as crystals.

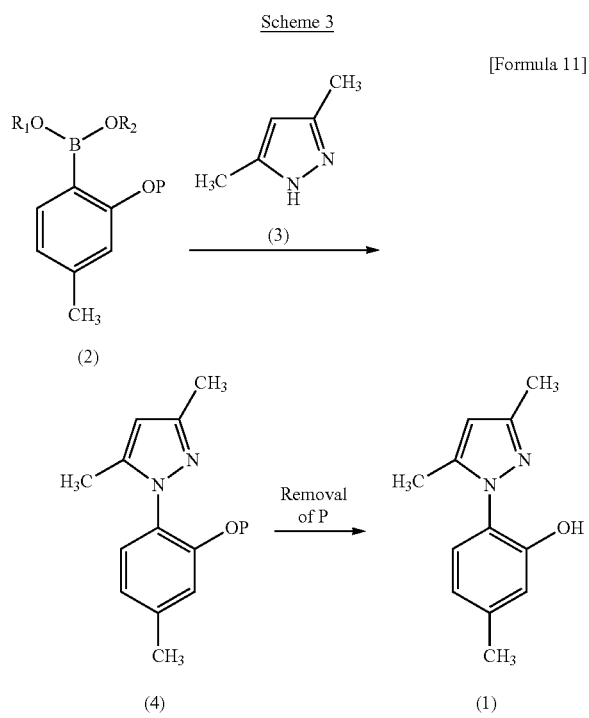

Scheme 3 in the Scheme, $R_1$ and $R_2$ each independently represent a hydrogen or a $C_{1-6}$ alkyl, or $R_1$ and $R_2$ are combined together to form a linear or branched $C_{2-6}$ alkylene, and P represents a hydrogen atom or a protective group for a hydroxy group.

The compound represented by the formula (2) can be obtained by referring to the method described in JP 2002-522545 A.

$R_1$ and $R_2$ each independently represent a hydrogen or a $C_{1-6}$ alkyl, or $R_1$ and $R_2$ are combined together to form a linear or branched $C_{2-6}$ alkylene. $R_1$ and $R_2$ are preferably combined together to form a linear or branched $C_{2-6}$ alkylene, further preferably $R_1$ and $R_2$ are combined together to form a 2,3-dimethylbutan-2,3-diyl group.

In addition, when $R_1$ and $R_2$ are hydrogens, after the compound of the formula (2) is reacted with a $C_{1-6}$ alcohol or a diol such as ethylene glycol, propan-di-ol, pinacol, etc., in the reaction, the resulting material may be used for the reaction with the compound of the formula (3) as it is.

P in the formula (2) is a hydrogen atom or may use a protective group for a hydroxy group well known to those skilled in the art, preferably a hydrogen atom, a methoxymethyl group or a tetrahydropyranyl group.

A catalyst may be used in the reaction of the compound of the formula (2) with the compound of the formula (3). As the catalyst, a copper reagent such as copper(II) acetate, copper(II) acetate hydrate, acetylacetone copper(II), copper (I) oxide, etc., can be used. It is preferably copper(II) acetate. In addition, when these catalysts are used, there is a case where good results may be obtained by reacting the materials in the presence of oxygen or an air.

An amount of the catalyst to be used based on an amount of the compound of the formula (2) is not particularly limited if it is an amount to proceed the reaction. It may be varied depending on the kind of the catalyst, and in the point of securing a sufficient reaction rate, it is preferably 0.01 to 5 equivalent, more preferably 0.5 to 2 equivalent.

An amount of the compound of the formula (3) to be used based on an amount of the compound of the formula (2) is not particularly limited if it is an amount to proceed the reaction, and it is preferably 0.2 to 100 equivalent, more preferably 1 to 5 equivalent.

The reaction solvent to be used in the reaction of the above-mentioned Scheme 3 is not particularly limited if it can proceed the reaction, and it may be a single solvent or a solvent in which several kinds of solvents are mixed. A mixing ratio of the solvents to be used may employ any ratio. N,N-dimethylformamide, tetrahydrofuran, chloroform, methylene chloride, acetonitrile, methanol, ethanol, 2-propanol, dimethylsulfoxide, etc., can be used, and preferably a mixed solvent of N,N-dimethylformamide and ethyl acetate.

In the reaction of the above-mentioned Scheme 3, it is preferred to add an organic base such as pyridine, bipyridine, diisopropylethylamine, triethylamine, diazabicycloundecene, etc., or an inorganic base such as potassium carbonate, cesium carbonate, etc., but the organic base or the inorganic base may not be added. When the base is to be added, an amount to be added is preferably in the range of 0.2 to 100 equivalent based on an amount of the compound of the formula (2), further preferably in the range of 1 to 10 equivalent.

A reaction temperature of the above-mentioned Scheme 3 is not particularly limited if it is a boiling point of the solvent to be used or lower and the reaction proceeds, and it is preferably 20 to 150° C., more preferably 20 to 100° C.

When P in the formula (2) is a protective group for a hydroxy group, after completion of the reaction of the compound of the formula (2) with the compound of the formula (3), the protective group is removed by the method in accordance with the kind of P, whereby it can be made the compound of the formula (1). Also, before the reaction with the compound of the formula (3), P is removed from the compound of the formula (2), and then it may be reacted with the compound of the formula (3) to prepare the compound of the formula (1). The method for removing the protective group P is known to those skilled in the art depending on the kind of P.

More preferred embodiment may be mentioned that pinacol is reacted with the compound where $R_1$, $R_2$ and P in the compound of the formula (2) are hydrogen atoms in the reaction to prepare a compound wherein $R_1$ and $R_2$ of the compound of the formula (2) are combined together to form a 2,3-dimethylbutan-2,3-diyl group, and the compound of the formula (3) (5 equivalent) as well as anhydrous copper (II) acetate and N,N-dimethylformamide are added thereto, and the resulting mixture is stirred from an ambient temperature to 65° C. to give the compound of the formula (1).

In addition, in one embodiment of the present invention, the compound of the formula (1) can be preferably prepared by the method of the following Scheme, and the compound of the formula (1) can be obtained as crystals.

Scheme 4

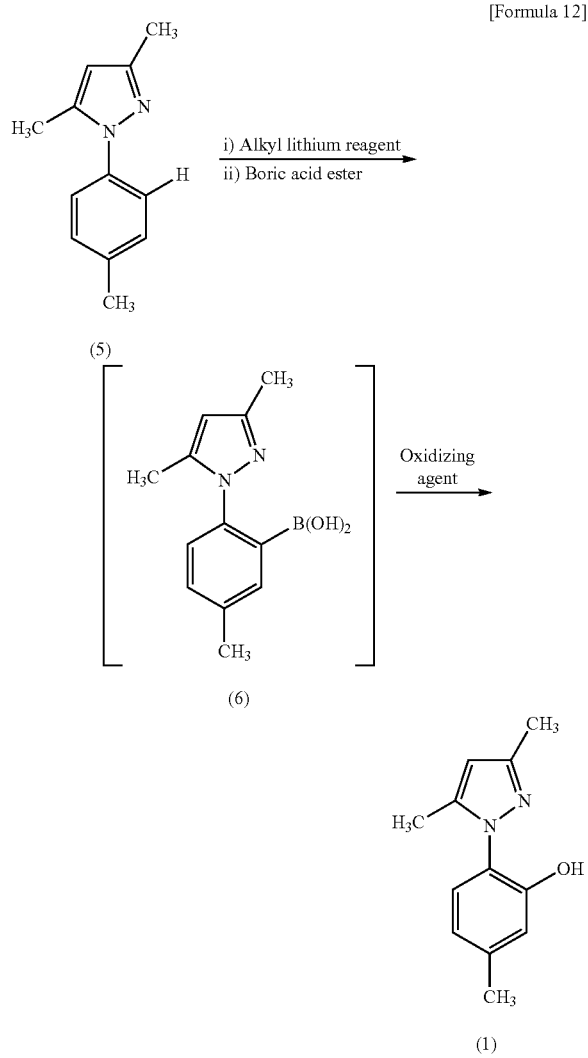

The compound of the formula (5) can be obtained by the methods disclosed in Justus Liebigs Annalen der Chemie, 1962, vol. 656, p. 119-126, and Helvetica Chimica Acta, 2010, vol. 93, p. 974-979. The compound of the formula (1) can be obtained by reacting an alkyl lithium reagent with the compound of the formula (5), then reacting with a boric acid ester to give a compound of the formula (6), and acting an oxidizing agent thereon.

The solvent to be used in the reaction from the formula (5) to the formula (6) is not particularly limited so long as the reaction proceeds, and there may be used an ether such as diethyl ether, 1,2-dimethoxyethane, tetrahydrofuran and dioxane, etc., and an aliphatic hydrocarbon such as n-pentane, n-hexane, n-heptane and cyclohexane, etc., and any mixed solvent comprising the above, etc. Preferred solvent is tetrahydrofuran.

The alkyl lithium reagent which can be used may be mentioned methyl lithium, n-butyl lithium, n-hexyl lithium, sec-butyl lithium, tert-butyl lithium, etc. It is preferably n-butyl lithium. An amount of the alkyl lithium reagent to be used is not particularly limited so long as the reaction proceeds. It is preferably 1.1 to 1.5 equivalent. A temperature when the alkyl lithium reagent is to be reacted is not particularly limited so long as it is a temperature at which the reaction proceeds, and preferably −5 to 0° C.

The boric acid ester which can be used may be mentioned trimethyl borate, triethyl borate, tripropyl borate, triisopropyl borate, tributyl borate, tri-tert-butyl borate, 2-Methoxy-4,4,5,5-tetramethyl-1,3,2-dioxaborolane, 2-Isopropoxy-4,4,5,5-tetramethyl-1,3,2-dioxaborolane, etc. It is preferably triisopropyl borate. An amount of the boric acid ester to be used is not particularly limited so long as the reaction proceeds, and preferably 1.5 to 3.0 equivalent. A temperature when the boric acid ester is to be reacted is not particularly limited so long as it is a temperature at which the reaction proceeds, and preferably 0 to 10° C.

The oxidizing agent to be used in the reaction from the formula (6) to the formula (1) which can be used may be mentioned potassium peroxymonosulfate, for example, OXONE (Registered Trademark), as well as hydrogen peroxide water, peracetic acid, m-chloroperbenzoic acid, tert-butylhydroperoxide, sodium perborate, and hydroxylamine, etc. It is preferably potassium peroxymonosulfate, in particular, OXONE (Registered Trademark). The solvent to be used may vary depending on the kind of the oxidizing agent to be used, and in the case of potassium peroxymonosulfate, water and an organic solvent such as acetone, acetonitrile, methanol, ethanol, 1-propanol, 2-propanol, methyl ethyl ketone, tetrahydrofuran, dioxane, N,N-dimethylformamide, dimethylsulfoxide, etc., may be used by mixing these solvents, preferably a mixed solvent of water and acetone. An amount of the oxidizing agent to be used is not particularly limited so long as the reaction proceeds, and preferably 1.0 to 1.2 equivalent. A temperature when the oxidizing agent is to be reacted is not particularly limited so long as it is a temperature at which the reaction proceeds, and preferably 0 to 25° C.

After completion of the reactions of the above-mentioned Scheme 3 and Scheme 4, the reaction treatment well known to those skilled in the art, for example, separation of liquids, concentration, solvent substitution, etc., were carried out, and a crude product of the compound of the formula (1) was made a 2-propanol solution. When water was added to the solution and the mixture was stirred, then a solid was precipitated. As a result of subjecting to powder X-ray diffraction measurement of the solid thus obtained, diffraction peaks were detected (FIG. 1). From the results mentioned above, the obtained solid was considered to be crystals.

In the following, characteristics of the crystals of the compound of the formula (1) are explained. The crystals mentioned herein mean a solid wherein atoms or molecules are periodically arranged solid, which is distinguished from a solid (amorphous) not having such a periodical arrangement. The crystals of the present invention mean crystals of 2-(3,5-dimethyl-1H-pyrazol-1-yl)-5-methylphenol, or may be an amorphous of 2-(3,5-dimethyl-1H-pyrazol-1-yl)-5-methylphenol which contains the crystals of 2-(3,5-dimethyl-1H-pyrazol-1-yl)-5-methylphenol.

1. Powder X-ray Diffraction Pattern

The crystals (Form A) of the compound of the formula (1) show their characteristic peaks of at least 5, preferably at least 10, more preferably 11, among the following diffraction angles in a powder X-ray diffraction pattern using a transmission type diffraction device.

Diffraction angles (2θ±0.2): 9.3°, 12.7°, 16.6°, 17.3°, 17.9°, 19.2°, 21.3°, 21.6°, 21.9°, 24.2°, 25.7°

Figure 2:
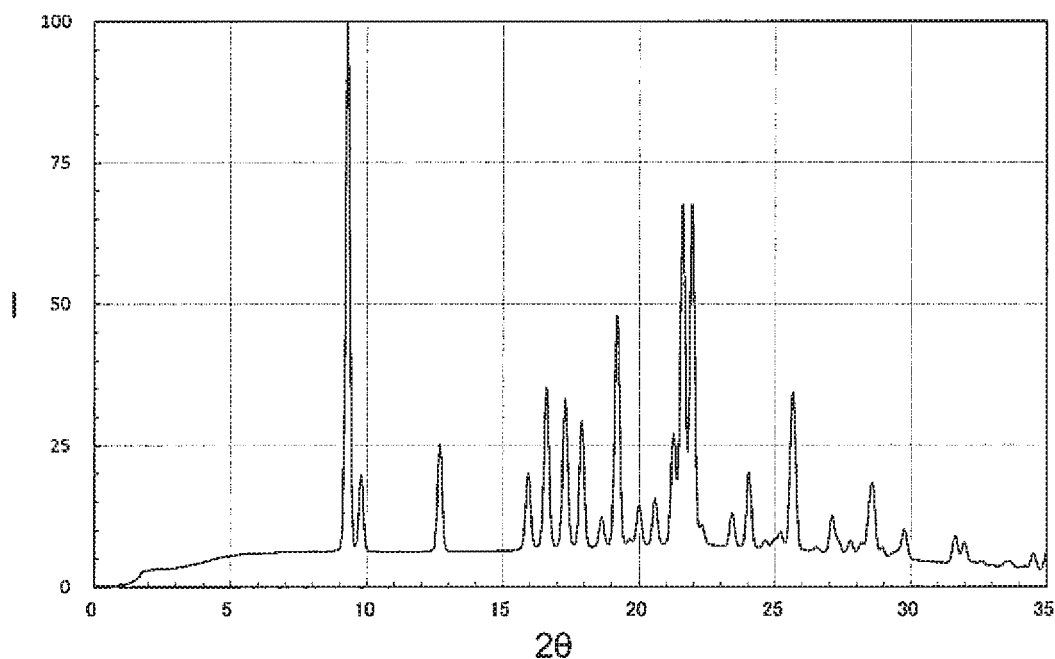
FIG. 2 is a drawing showing a powder X-ray diffraction pattern of Form A of the formula (1), which shows that even when the compounds of the formula (1) have the same crystal form, they show patterns having different intensities depending on the difference in lots or sampling.

In FIG. 1, a powder X-ray diffraction pattern of the crystals (Form A) of the compound of the formula (1) by the transmission type diffraction device was shown. When they are crystals of the compound of the formula (1), and any substances having essentially the same powder X-ray diffraction pattern as these diffraction patterns are identified as the crystals (Form A) of the compound of the formula (1). For example, due to the difference in lots of the samples to be measured, or even in the same lot, due to the conditions of sampling, a pattern different in intensities (FIG. 2) is sometimes shown. However, since FIG. 2 is essentially the same as the above-mentioned diffraction pattern, the crystal form can be understood to be Form A.

The crystals of the compound of the formula (1) according to the present invention can be made a pharmaceutical composition for anti-trichophyton by mixing with a pharmaceutically acceptable carrier. The pharmaceutically acceptable carrier may be mentioned various kinds of organic or inorganic carrier substances which are commonly used as a material for a formulation, for example, an excipient, a lubricant, a binder and a disintegrating agent in the solid formulation; and a solvent, a solubilizing agent, a suspending agent, an isotonizing agent, a buffer, a soothing agent, etc., in the liquid formulation. In addition, where necessary, a commonly used additive such as a preservative agent, an anti-oxidant, a coloring agent, a sweetening agent, an adsorbent, a humectant, etc., may be used.

A pharmaceutical composition comprising crystals of the compound of the formula (1) according to the present invention can be administered to human and animals other than human through any administration route of oral or parenteral (for example, percutaneous administration).

The pharmaceutical composition comprising crystals of the compound of the formula (1) according to the present invention can be made a suitable dosage form depending on an administration route. Specifically, it may be formulated to a dosage form including an oral preparation such as a capsule, a tablet, a granule, a powder, a pill, a fine granule, etc., or an external preparation such as a patch, a liquid formulation, etc.

EXAMPLES

Examples of the present invention are shown in the following, but the present invention is not limited to the Examples mentioned below.

Powder X-ray Diffraction (Transmission Method):

Using high-speed imaging plate X-ray diffraction system (R-AXIS VII) manufactured by Rigaku Corporation, X-ray diffraction data of the crystals of the compound of the formula (1) were measured at −180° C. with a CuK α radiation (50 kV, 90 mA, λ=1.5418 Å). A sample was filled in a glass capillary having an inner diameter of 0.7 mm. The diffraction images were collected under the conditions a camera length of 300 mm, an oscillation angle of 40°, and an exposure time of 45 minutes.

A contour integration treatment of the diffraction image was carried out by an R-AXIS display software available from Rigaku Corporation (integration range: 45 to 135°). The maximum value of the obtained integrated intensity was made 100, relative intensities of the respective integral intensities were calculated, and plotting them based on the diffraction angle 2θ to prepare a diffraction pattern.

Preparation of 2-(3,5-dimethyl-1H-pyrazol-1-yl)-5-methylphenol (formula (1)) and preparation of crystals Example 1: Preparation of 2-(3,5-dimethyl-1H-pyrazol-1-yl)-5-methylphenol 1) To 25.6 g of 3,5-dimethyl-1-(4-methylphenyl)-1H-pyrazole was added 390 mL of dehydrated tetrahydrofuran, and the mixture was cooled under nitrogen atmosphere to −5 to 0° C. To the mixture was added dropwise 78 mL (1.5 equivalent) of an n-hexane solution containing 2.65M n-butyl lithium, and the mixture was stirred at −5 to 0° C. for one hour. To the mixture was added 64 mL (2.0 equivalent) of triisopropyl borate, and the mixture was stirred at 0 to 10° C. for 30 minutes. To the mixture was added 390 mL of a 10% ammonium chloride solution, and after adjusting a pH to 4.5 by 6M hydrochloric acid, the mixture was extracted with 390 mL of ethyl acetate, and the aqueous layer was removed. After the organic layer was washed with 240 mL of 15% brine, the organic layer was concentrated to 120 mL under reduced pressure. To the mixture was added 240 mL of acetone, the mixture was concentrated to 120 mL under reduced pressure to give an acetone solution of 2-{(3,5-dimethyl-1H-pyrazol-1-yl)-5-methylphenyl}boronic acid (formula (6)). 2-{(3,5-Dimethyl-1H-pyrazol-1-yl)-5-methylphenyl}boronic acid (6)

MS; m/z 231 (M+H)$^+$ 2) 330 mL of acetone was added to the acetone solution of 2-{(3,5-dimethyl-1H-pyrazol-1-yl)-5-methylphenyl}boronic acid obtained in 1), and the mixture was cooled to 0 to 5° C. To the mixture was added 550 mL (1.2 equivalent) of 0.3M aqueous solution of OXONE (Registered Trademark), and the mixture was stirred at 0 to 25° C. for 20 minutes. After cooling the mixture to 10° C. or lower, 240 mL of a 25% sodium sulfite solution was added thereto, and then 450 mL of toluene was added to the same. The suspension was filtered, then adjusted the pH to 5 with 6M hydrochloric acid, and the aqueous layer was removed. The organic layer was concentrated to 300 mL under reduced pressure, 300 mL of 1M sodium hydroxide solution was added thereto, and the organic layer was removed. The aqueous layer was washed with 60 mL of toluene, and adjusted the pH to 5 with 6M hydrochloric acid. The aqueous layer was extracted with 300 mL of ethyl acetate, and the aqueous layer was removed. The organic layer was washed with 150 mL of water. To the organic layer was added 3 g of activated charcoal, and the mixture was stirred for 15 minutes, filtered and concentrated to 60 mL under reduced pressure. To the residue was added 240 mL of 2-propanol, and the mixture was concentrated to 60 mL under reduced pressure. To the residue were added 60 mL of 2-propanol and 60 mL of water, the resulting mixture was cooled to 10° C. or lower to precipitate crystals, then 180 mL of water was added thereto, and the mixture was stirred. The crystals were filtered, washed with a mixed solution of 2-propanol and water, and then dried to give 21.3 g of a solid of 2-(3,5-dimethyl-1H-pyrazol-1-yl)-5-methylphenol.

$^1$H-NMR (400 MHz, CDCl$_3$) δ (ppm); 9.62 (1H, s), 7.07 (1H, d, J=8.0 Hz), 6.91 (1H, s), 6.71 (1H, d, J=8.0 Hz), 6.01 (1H, s), 2.37 (3H, s), 2.33 (3H, s), 2.29 (3H, s)

MS (ESI); m/z 203 (M+H)$^+$

As a result of measurement of powder X-ray diffraction, diffraction peaks were observed. The crystal form showing this powder diffraction pattern was termed Form A.

In the following, the products of Examples were compared with the analytical result of $^1$H-NMR of Example 1, and it was confirmed to be 2-(3,5-dimethyl-1H-pyrazol-1-yl)-5-methylphenol.

Example 2: Preparation of 2-(3,5-dimethyl-1H-pyrazol-1-yl)-5-methylphenol 7 mL of dehydrated tetrahydrofuran was added to 278.8 mg of 3,5-dimethyl-1-(4-methylphenyl)-1H-pyrazole, and the mixture was cooled to 0° C. under nitrogen atmosphere.

To the mixture was added dropwise a solution of 1.64M n-butyl lithium in n-hexane (1 mL; 1.1 equivalent), and the mixture was stirred at 0° C. for 30 minutes. To the mixture was added 0.5 mL (1.5 equivalent) of triisopropyl borate, and the mixture was stirred at 0° C. for one hour. To the mixture were added 7 mL of water and 20 mL of toluene, the mixture was adjusted the pH to 1.0 with 1M hydrochloric acid, and the mixture was stirred at room temperature for 30 minutes. The mixture was adjusted the pH to 4 with a 1M sodium hydroxide solution, and the aqueous layer was removed. After the organic layer was washed with 10 mL of 15% brine, the organic layer was concentrated under reduced pressure to give 318 mg of 2-{(3,5-dimethyl-1H-pyrazol-1-yl)-5-methylphenyl}boronic acid.

5 mL of acetone was added to the 2-{(3,5-dimethyl-1H-pyrazol-1-yl)-5-methylphenyl}boronic acid, and the mixture was cooled to 0 to 5° C. To the mixture was added 5 mL (1.0 equivalent) of a 0.3M aqueous OXONE (Registered Trademark) solution, and the mixture was stirred at 15 to 25° C. for 35 minutes. After cooling the mixture to 10° C. or lower, to the mixture were added 10 mL of a saturated sodium sulfite solution and 20 mL of ethyl acetate, and the aqueous layer was removed. To the organic layer was added 10 mL of a saturated sodium sulfite solution, and the aqueous layer was removed. To the organic layer was added 10 mL of 15% brine, and the aqueous layer was removed. The organic layer was concentrated under reduced pressure to give 243 mg of a crude product of 2-(3,5-dimethyl-1H-pyrazol-1-yl)-5-methylphenol.

To 207 mg of the crude product of 2-(3,5-dimethyl-1H-pyrazol-1-yl)-5-methylphenol were added 0.8 mL of 2-propanol and 0.4 mL of water, the mixture was cooled to 10° C. or lower to precipitate a solid, 1.3 mL of water was added thereto, and the mixture was stirred. The solid was filtered, washed with a mixed solution of 2-propanol and water, and dried to give 160 mg of a crystalline solid of 2-(3,5-dimethyl-1H-pyrazol-1-yl)-5-methylphenol.

Example 3: Preparation of
2-(3,5-dimethyl-1H-pyrazol-1-yl)-5-methylphenol 40 mL of dehydrated tetrahydrofuran was added to 2.65 g of 3,5-dimethyl-1-(4-methylphenyl)-1H-pyrazole, and the mixture was cooled to 0° C. under nitrogen atmosphere. To the mixture was added dropwise a solution of 1.64M n-butyl lithium in n-hexane (13.0 mL; 1.5 equivalent), and the mixture was stirred at 0° C. for 30 minutes. To the mixture was added 6.6 mL (2.0 equivalent) of triisopropyl borate, and the mixture was stirred at 0° C. for one hour. To the mixture was added 40 mL of a 10% ammonium chloride solution, the mixture was adjusted the pH to 4 with 2M hydrochloric acid and extracted with 53 mL of ethyl acetate, and the aqueous layer was removed. The organic layer was washed with 27 mL of 15% brine, and the organic layer was concentrated under reduced pressure to give 3.45 g of 2-{(3,5-dimethyl-1H-pyrazol-1-yl)-5-methylphenyl}boronic acid.

48 mL of acetone was added to the 2-{(3,5-dimethyl-1H-pyrazol-1-yl)-5-methylphenyl}boronic acid, and the mixture was cooled to 0 to 5° C. To the mixture was added 48 mL (1.0 equivalent) of a 0.3M aqueous OXONE (Registered Trademark) solution, and the mixture was stirred at 15 to 25° C. for 30 minutes. After cooling the mixture to 10° C. or lower, to the mixture were added 40 mL of a 15% sodium sulfite solution and 40 mL of toluene. The suspension was filtered, and the aqueous layer was removed. To the organic layer was added 27 mL of 15% brine, and the aqueous layer was removed.

The organic layer was concentrated to 27 mL under reduced pressure, 27 mL of a 1M sodium hydroxide solution was added thereto, and the organic layer was removed. The aqueous layer was adjusted the pH to 5 with 2M hydrochloric acid. The aqueous layer was extracted with 27 mL of ethyl acetate, and the aqueous layer was removed. The organic layer was washed with 13 mL of water. To the organic layer was added 0.27 g of activated charcoal, and the mixture was stirred for 10 minutes, filtered and concentrated to 5 mL under reduced pressure.

To the residue was added 21 mL of 2-propanol, and the mixture was concentrated to 5 mL under reduced pressure. To the residue were added 5 mL of 2-propanol and 5 mL of water, and the mixture was cooled to 10° C. or lower to precipitate a solid, then 16 mL of water was added thereto, and the mixture was stirred. The solid was filtered, washed with a mixed solution of 2-propanol and water, and dried to give 2.54 g of a crystalline solid of 2-(3,5-dimethyl-1H-pyrazol-1-yl)-5-methylphenol.

Example 4: Preparation of
2-(3,5-dimethyl-1H-pyrazol-1-yl)-5-methylphenol

1) In 200 mL of heptane was dissolved 20.070 g of m-cresol, to the solution were added 25.4 mL of dihydropyran and 446 mg of pyridinium p-toluenesulfonate under room temperature, and the mixture was stirred overnight. To the solution was added 3.8 mL of 1M sodium methoxide, and the mixture was stirred under room temperature for 30 minutes. To the solution was added 100 mL of a 1M aqueous sodium hydroxide solution, the organic layer was separated, and the obtained organic layer was washed with 20% brine. The obtained organic layer was dried over anhydrous sodium sulfate, the drying agent was filtered off, and the filtrate was concentrated under reduced pressure to give 33.497 g of a crude product of 2-(m-tolyloxy)tetrahydro-2H-pyrane.

$^1$H-NMR (400 MHz, CDCl$_3$) δ (ppm); 7.16 (1H, dd, J=7.8, 7.8 Hz), 6.85-6.87 (2H, m), 6.80 (1H, d, J=7.3 Hz), 5.41 (1H, dd, J=3.2, 3.2 Hz), 3.89-3.95 (1H, m), 3.57-3.62 (1H, m), 2.33 (3H, s), 1.96-2.03 (1H, m), 1.83-1.87 (2H, m), 1.58-1.72 (3H, m)

2) In 670 mL of tetrahydrofuran was dissolved the whole amount of the crude product of 2-(m-tolyloxy)tetrahydro-2H-pyrane obtained in 1), 158 mL of 1.6M n-butyl lithium was added dropwise thereto at 0° C., and the mixture was stirred at the temperature for 30 minutes. To the solution was added 56.3 mL of triisopropyl borate at 0° C., and the mixture was further stirred at the temperature for one hour. To the solution was added 150 mL of 2M hydrochloric acid, and the mixture was further stirred under room temperature overnight. To the solution was added 300 mL of isopropyl ether, the organic layer was separated, and the obtained organic layer was washed with 150 mL of 2M hydrochloric acid. The obtained organic layer was dried over anhydrous magnesium sulfate, the drying agent was filtered off, and the filtrate was concentrated under reduced pressure. To the residue was added 500 mL of hexane, and the formed solid was filtered and dried to give 15.197 g of a crude product of (2-hydroxy-4-methylphenyl)boronic acid.

3) In 200 mL of ethyl acetate were dissolved 20.045 g of a crude product of (2-hydroxy-4-methylphenyl)boronic acid and 31.178 g of pinacol, and the mixture was stirred under room temperature. The reaction mixture was concentrated under reduced pressure, and the obtained residue was dissolved in 100 mL of ethyl acetate. The solution was added dropwise at 65° C. to a solution in which 63.402 g of 1,3-dimethylpyrazole and 23.959 g of anhydrous copper(II) acetate had been dissolved in 400 mL of N,N-dimethylformamide, thereafter, the mixture was stirred at room temperature to 65° C. To the solution were added 400 mL of ethyl acetate and 400 mL of 20% brine, and the organic layer was separated. The obtained organic layer was washed twice with 400 mL of 20% brine, and further washed twice with 400 mL of a 15% aqueous Rochelle salt solution. To the obtained organic layer were added 100 g of magnesium sulfate and 4 g of activated charcoal, and then the mixture was stirred and filtered. The obtained filtrate was subject to solvent substitution and concentration with toluene under reduced pressure, and to the obtained toluene solution was added 400 mL of a 1M aqueous sodium hydroxide solution. The aqueous layer was separated and washed with 400 mL of toluene. To the obtained aqueous layer was added 400 mL of ethyl acetate, and the mixture was adjusted the pH to 5.9 with 6M hydrochloric acid. The obtained organic layer was subject to solvent substitution and concentration with 2-propanol under reduced pressure, and then water was added thereto to precipitate a solid. The obtained solid was filtered and dried to give 18.249 g of a crystalline solid of 2-(3,5-dimethyl-1H-pyrazol-1-yl)-5-methylphenol.

As a result of measurement of powder X-ray diffraction, it was confirmed to be Form A.

Example 5: Preparation of
2-(3,5-dimethyl-1H-pyrazol-1-yl)-5-methylphenol

1) In 100 mL of methylene chloride was dissolved 10.040 g of m-cresol, to the solution were added 37 mL of formaldehyde dimethyl acetal and 88 mg of p-toluenesulfonic acid, and the mixture was refluxed with heating for 24 hours. To the solution was added 1 mL of 1M sodium methoxide, the reaction mixture was concentrated under reduced pressure, the obtained residue was diluted with 200 mL of heptane, and 200 mL of a 1M aqueous sodium hydroxide solution was added thereto. The organic layer was separated, the obtained organic layer was washed with 200 mL of 20% brine, and the obtained organic layer was dried over anhydrous sodium sulfate. The drying agent was filtered off, and the filtrate was concentrated under reduced pressure to give 5.602 g of a crude product of 1-(methoxymethoxy)-3-methylbenzene.

2) In 5 mL of tetrahydrofuran was dissolved 506 mg of the crudely purified product of 1-(methoxymethoxy)-3-methylbenzene, to the solution was added dropwise 2.22 mL of 1.6M n-butyl lithium at 0° C., and the mixture was stirred at the temperature for 50 minutes. To the solution was added at 0° C. the solution in which 0.848 mL of triisopropyl borate had been dissolved in 5 mL of tetrahydrofuran, and the mixture was further stirred at the temperature for 2 hours. To the solution was added at 0° C. the solution in which 864 mg of pinacol had been dissolved in 5 mL of tetrahydrofuran, a temperature of the mixture was raised to room temperature, and the mixture was stirred. The obtained solution was diluted with 30 mL of ethyl acetate, and 30 mL of a 20% aqueous ammonium chloride solution was added thereto. The organic layer was separated, and the aqueous layer was extracted with ethyl acetate again. The obtained organic layers were combined, washed with 30 mL of 20% brine, and the obtained organic layer was dried over anhydrous sodium sulfate. The drying agent was filtered off, and the filtrate was concentrated under reduced pressure to give 1.095 g of a crude product of 2-(2-(methoxymethoxy)-4-methylphenyl)-4,4,5,5-tetramethyl-1,3,2-dioxaborolane.

3) In 12 mL of 2-propanol were dissolved 744 mg of the crude product of 2-(2-(methoxymethoxy)-4-methylphenyl)-4,4,5,5-tetramethyl-1,3,2dioxaborolane, 1.029 g of 1,3-dimethylpyrazole and 12 mg of anhydrous copper(II) acetate, and the mixture was stirred under room temperature. Insoluble materials were filtered off, the insoluble materials were further washed with ethyl acetate, and the filtrate was concentrated under reduced pressure. To the residue were added ethyl acetate and a 15% aqueous Rochelle salt solution, the organic layer was decanted, and the obtained organic layer was further washed with a 15% aqueous Rochelle salt solution. The obtained organic layer was concentrated under reduced pressure to give a crude product of 1-(2-(methoxymethoxy)-4-methylphenyl)-3,5-dimethyl-1H-pyrazole. The product was dissolved in 4 mL of 2-propanol, 2 mL of 6M hydrochloric acid water was added thereto, and the resulting mixture was stirred under room temperature. The mixture was diluted with water, and adjusted the pH to 1.3 with a 1M aqueous sodium hydroxide solution. The organic layer was separated, the aqueous layer was further extracted with ethyl acetate three times, the obtained organic layers were quantitated, and then 144 mg of 2-(3,5-dimethyl-1H-pyrazol-1-yl)-5-methylphenol was obtained.

Example 6: Preparation of
2-(3,5-dimethyl-1H-pyrazol-1-yl)-5-methylphenol

In 8.5 mL of tetrahydrofuran was dissolved a crude product of 2-(m-tolyloxy)tetrahydro-2H-pyrane synthesized from 505 mg of m-cresol. To the solution was added 3.23 mL of 1.6M n-butyl lithium at 0° C., and the mixture was stirred under room temperature overnight. To the solution was added 1.41 mL of triisopropyl borate at 0° C., and a temperature of the mixture was further raised to room temperature. To the solution was added a solution of 1.103 g of pinacol in 0.5 mL of tetrahydrofuran. To the solution were added 4.489 g of 1,3-dimethylpyrazole and 848 mg of anhydrous copper(II) acetate. To the suspension were further added 10 mL of tetrahydrofuran and 848 mg of anhydrous copper(II) acetate, and the mixture was stirred under room temperature overnight. To the suspension were added 12 ml of 2M hydrochloric acid and 6 mL of 6M hydrochloric acid, and the mixture was stirred under room temperature for 3 hours. Insoluble materials were filtered off, and the insoluble materials were further washed with ethyl acetate, a 15% aqueous Rochelle salt solution was added thereto, and the organic layer was separated. The aqueous layer was further extracted with ethyl acetate three times, the obtained organic layers were quantitated, and then 212 mg of 2-(3,5-dimethyl-1Hpyrazol-1-yl)-5-methylphenol was obtained.

Example 7: Preparation of
2-(3,5-dimethyl-1H-pyrazol-1-yl)-5-methylphenol

In 10 mL of ethanol were dissolved 504 mg of the crude product of (2-hydroxy-4-methylphenyl)boronic acid and 1.594 g of 1,3-dimethylpyrazole, 1.324 g of copper(II) acetate dihydrate was added to the solution. Further, 5 mL of ethanol and 2.3 mL of triethylamine dissolved in 5 mL of ethanol were added to the solution, and the mixture was stirred under room temperature. The mixture was diluted with ethyl acetate, 130 mL of a 0.1M aqueous EDTA solution was added thereto, and the precipitated was filtered off. The organic layer was separated, the aqueous layer was extracted with ethyl acetate three times, the obtained organic layers were quantitated, and then 208 mg of 2-(3,5-dimethyl-III-pyrazol-1-yl)-5-methylphenol was obtained.

Example 8: Preparation of 2-(3,5-dimethyl-1H-pyrazol-1-yl)-5-methylphenol

In 1 mL of 2-propanol were suspended 37 mg of the crude product of (2-hydroxy-4-methylphenyl)boronic acid and 117 mg of 1,3-dimethylpyrazole, 97 mg of copper(II) acetate dihydrate was added thereto, to the suspension were further added 1 mL of 2-propanol and 0.17 mL of triethylamine, and the mixture was stirred under room temperature. The obtained solution was diluted with ethyl acetate, and a 15% aqueous Rochelle salt solution was added thereto. The organic layer was separated, the organic layer was washed with a 15% aqueous Rochelle salt solution, the obtained organic layer was quantitated, and then 208 mg of 2-(3,5-dimethyl-1H-pyrazol-1-yl)-5-methylphenol was obtained.

Example 9: Preparation of 2-(3,5-dimethyl-1H-pyrazol-1-yl)-5-methylphenol

In 1 mL of tetrahydrofuran were dissolved 27 mg of the crude product of (2-hydroxy-4-methylphenyl)boronic acid and 85 mg of 1,3-dimethylpyrazole, 71 mg of copper(II) acetate dihydrate was added thereto, further 1 mL of tetrahydrofuran and 0.12 mL of triethylamine were added to the same, and the mixture was stirred under room temperature. The mixture was diluted with ethyl acetate, and a 15% aqueous Rochelle salt solution was added thereto. Insoluble materials were filtered off, the organic layer was separated, the aqueous layer was extracted with ethyl acetate three times, the obtained organic layers were quantitated, and then 15 mg of 2-(3,5-dimethyl-1H-pyrazol-1-yl)-5-methylphenol was obtained.

Example 10: Preparation of 2-(3,5-dimethyl-1H-pyrazol-1-yl)-5-methylphenol

In 2 mL of 2-propanol were suspended 26 mg of a crude product of (2-hydroxy-4-methylphenyl)boronic acid, 82 mg of 1,3-dimethylpyrazole and 68 mg of copper(II) acetate dihydrate, to the suspension was added 0.15 mL of diisopropylethylamine, and the mixture was stirred under room temperature. Insoluble materials were filtered off the obtained organic layer was quantitated, and then 14 mg of 2-(3,5dimethyl-1H-pyrazol-1-yl)-5-methylphenol was obtained.

Example 11: Preparation of 2-(3,5-dimethyl-H-pyrazol-1-yl)-5-methylphenol

In 1 mL of 2-propanol were suspended 28 mg of a crude product of (2-hydroxy-4-methylphenyl)boronic acid and 177 mg of 1,3-dimethylpyrazole, to the suspension were added 74 mg of copper(II) acetate dihydrate, 1 mL of 2-propanol and 0.16 mL of diisopropylethylamine, and the mixture was stirred under room temperature overnight. Insoluble materials were filtered off, the obtained organic layer was quantitated, and then 19 mg of 2-(3,5-dimethyl-1H-pyrazol-1-yl)-5-methylphenol was obtained.

Example 12: Preparation of 2-(3,5-dimethyl-1H-pyrazol-1-yl)-5-methylphenol

In 4 mL of dehydrated 2-propanol were suspended 98 mg of a crude product of (2-hydroxy-4-methylphenyl)boronic acid, 645 mg of 1,3-dimethylpyrazole and 234 mg of anhydrous copper(II) acetate, then 0.56 mL of diisopropylethylamine was added to the suspension, and the mixture was stirred at 65° C. overnight. When the obtained organic layer was quantitated, then 54 mg of 2-(3,5-dimethyl-1H-pyrazol-1-yl)-5-methylphenol was obtained.

Example 13: Preparation of 2-(3,5-dimethyl-1H-pyrazol-1-yl)-5-methylphenol

In 2 mL of 2-propanol were suspended 26 mg of a crude product of (2-hydroxy-4-methylphenyl)boronic acid, 82 mg of 1,3-dimethylpyrazole, 68 mg of copper(II) acetate dihydrate, then 0.13 mL of diazabicycloundecene was added to the suspension, and the mixture was stirred under room temperature. Insoluble materials were filtered off, the obtained organic layer was quantitated, and then 7 mg of 2-(3,5-dimethyl-1H-pyrazol-1-yl)-5-methylphenol was obtained.

Example 14: Preparation of 2-(3,5-dimethyl-1H-pyrazol-1-yl)-5-methylphenol

In 1 mL of ethanol were dissolved 23 mg of a crude product of (2-hydroxy-4-methylphenyl)boronic acid and 73 mg of 1,3-dimethylpyrazole, and to the solution were added 60 mg of copper(II) acetate dihydrate and 1 mL of ethanol. To the mixture was added 0.13 mL of diisopropylethylamine, and the mixture was stirred under room temperature overnight. Insoluble materials were filtered off, the obtained organic layer was quantitated, and then 10 mg of 2-(3,5-dimethyl-1H-pyrazol-1-yl)-5-methylphenol was obtained.

Example 15: Preparation of 2-(3,5-dimethyl-1H-pyrazol-1-yl)-5-methylphenol

In 1 mL of acetonitrile were dissolved 23 mg of the crude product of (2-hydroxy-4-methylphenyl)boronic acid and 73 mg of 1,3-dimethylpyrazole, and to the solution were added 60 mg of copper(II) acetate dihydrate and 1 mL of acetonitrile. To the mixture was added 0.13 mL of diisopropylethylamine and the mixture was stirred under room temperature overnight. Insoluble materials were filtered off, the obtained organic layer was quantitated, and then 12 mg of 2-(3,5-dimethyl-1H-pyrazol-1-yl)-5-methylphenol was obtained.

Example 16: Preparation of 2-(3,5-dimethyl-1H-pyrazol-1-yl)-5-methylphenol

In 1 mL of methylene chloride were dissolved 23 mg of the crude product of (2-hydroxy-4-methylphenyl)boronic acid and 85 mg of 1,3-dimethylpyrazole, and to the solution were added 71 mg of copper(II) acetate dihydrate and 1 mL of methylene chloride. To the mixture was added 0.13 mL of diisopropylethylamine, and the mixture was stirred under room temperature overnight. Insoluble materials were filtered off the obtained organic layer was quantitated, and then 11 mg of 2-(3,5-dimethyl-1H-pyrazol-1-yl)-5-methylphenol was obtained.

Example 17: Preparation of 2-(3,5-dimethyl-1H-pyrazol-1-yl)-5-methylphenol

In 1.5 mL of methylene chloride were suspended Molecular Sieves 4A, 35 mg of the crude product of (2-hydroxy-4-methylphenyl)boronic acid and 111 mg of 1,3-dimethylpyrazole, and to the suspension were added 92 mg of copper(II) acetate dihydrate and 0.5 mL of methylene chloride. To the mixture was added 0.2 mL of diisopropylethylamine, and the mixture was stirred under room temperature overnight.

Insoluble materials were filtered off, the obtained organic layer was quantitated, and then 7 mg of 2-(3,5-dimethyl-1H-pyrazol-1-yl)-5-methylphenol was obtained.

Example 18: Preparation of 2-(3,5-dimethyl-1H-pyrazol-1-yl)-5-methylphenol 2 mL of tetrahydrofuran was added to a mixture of 27 mg of a crude product of (2-hydroxy-4-methylphenyl)boronic acid, 171 mg of 1,3-dimethylpyrazole and 71 mg of copper(II) acetate dihydrate, and the resulting mixture was stirred under room temperature. Insoluble materials were filtered off, the obtained organic layer was quantitated, and then 7 mg of 2-(3,5-dimethyl-1H-pyrazol-1-yl)-5-methylphenol was obtained.

Example 19: Preparation of 2-(3,5-dimethyl-1H-pyrazol-1-yl)-5-methylphenol 2 mL of methylene chloride was added to a mixture of 29 mg of a crude product of (2-hydroxy-4-methylphenyl)boronic acid, 184 mg of 1,3-dimethylpyrazole and 76 mg of copper(II) acetate dihydrate, and the resulting mixture was stirred under room temperature overnight. Insoluble materials were filtered off, the obtained organic layer was quantitated, and then 6 mg of 2-(3,5-dimethyl-1H-pyrazol-1-yl)-5-methylphenol was obtained.

Example 20: Preparation of 2-(3,5-dimethyl-1H-pyrazol-1-yl)-5-methylphenol 2 mL of 2-propanol was added to a mixture of 27 mg of a crude product of (2-hydroxy-4-methylphenyl)boronic acid, 171 mg of 1,3-dimethylpyrazole and 71 mg of copper(II) acetate dihydrate, and the resulting mixture was stirred under room temperature. Insoluble materials were filtered off, the obtained organic layer was quantitated, and then 13 mg of 2-(3,5-dimethyl-1H-pyrazol-1-yl)-5-methylphenol was obtained.

Example 21: Preparation of 2-(3,5-dimethyl-1H-pyrazol-1-yl)-5-methylphenol 2 mL of 2-propanol was added to a mixture of 26 mg of the crude product of (2-hydroxy-4-methylphenyl)boronic acid, 164 mg of 1,3-dimethylpyrazole, 68 mg of copper(II) acetate dihydrate and 279 mg of cesium carbonate, and the resulting mixture was stirred under room temperature. Insoluble materials were filtered off, the obtained organic layer was quantitated, and then 2 mg of 2-(3,5-dimethyl-1H-pyrazol-1-yl)-5-methylphenol was obtained.

Example 22: Preparation of 2-(3,5-dimethyl-1H-pyrazol-1-yl)-5-methylphenol 2 mL of dimethylsulfoxide was added to a mixture of 27 mg of a cruded product of (2-hydroxy-4-methylphenyl)boronic acid, 171 mg of 1,3-dimethylpyrazole and 71 mg of copper(II) acetate dihydrate, and the resulting mixture was stirred under room temperature. The obtained organic layer was quantitated, and then 5 mg of 2-(3,5-dimethyl-1H-pyrazol-1-yl)-5-methylphenol was obtained.

Example 23: Preparation of 2-(3,5-dimethyl-1H-pyrazol-1-yl)-5-methylphenol

1) In 10 mL of ethanol was dissolved 5.047 g of 2-aminocresol, and 3.55 mL of conc. hydrochloric acid and 5 mL of ethanol were added thereto. The mixture was cooled to 0° C., and 5.62 mL of isoamyl nitrite was further added dropwise. This solution was added dropwise to a solution of 68.035 g of potassium iodide in 70 mL of water, cooled at −7.5° C., and then the temperature of the mixture was raised to room temperature. To the solution was added 15 mL of ethanol, and the mixture was further stirred under room temperature. The obtained solution was diluted with ethyl acetate, amylene was further added thereto, and the organic layer was separated. Further, the aqueous layer was extracted with ethyl acetate, and then the obtained organic layers were washed with 20% brine. The obtained organic layer was dried over magnesium sulfate, the drying agent was filtered off, and the filtrate was concentrated under reduced pressure. The residue was purified by silica gel chromatography to give 4.601 g of 2-iodo-5-methylphenol.

2) In 10 mL of 1,4-dioxane was dissolved 1.016 g of 2-iodo-5-methylphenol, a solution of 2.756 g of bispinacol diborane in 10 mL of 1,4-dioxane was further added thereto, and a solution of 2.130 g of potassium acetate in 10 mL of 1,4-dioxane was further added thereto. After replacing the atmosphere with nitrogen, 355 mg of palladium chloride complex of (diphenylphosphino)-ferrocene ([1,1'-Bis(diphenylphosphino)ferrocene]dichloropalladium(II)) was added to the mixture, and the resulting mixture was stirred at 95° C. After cooling to ambient temperature, insoluble materials were filtered off, and the filtrate was concentrated under reduced pressure. The residue was purified by silica gel chromatography to give 405 mg of 5-methyl-2-(4,4,5,5-tetramethyl-1,3,2-dioxaborolan)-2-yl)phenol.

$^1$H-NMR (400 MHz, CDCl$_3$) δ (ppm); 7.75 (1H, s), 7.49 (1H, d, J=8.2 Hz), 6.70-6.72 (2H, m), 2.32 (3H, s), 1.36 (12H, s), 6.01 (1H, s), 2.37 (3H, s), 2.33 (3H, s), 2.29 (3H, s)

3) 3 mL of 2-propanol was added to a mixture of 20 mg of 5-methyl-2-(4,4,5,5-tetramethyl-1,3,2-dioxaborolan)-2-yl)phenol, 82 mg of 1,3-dimethylpyrazole and 34 mg of copper(II) acetate dihydrate, then 0.074 mL of diisopropylethylamine was further added thereto, and the resulting mixture was stirred under room temperature. When the obtained organic layer was quantitated, then 11 mg of 2-(3,5-dimethyl-1H-pyrazol-1-yl)5-methylphenol was obtained.

Example 24: Preparation of 2-(3,5-dimethyl-1H-pyrazol-1-yl)-5-methylphenol 3 mL of 2-propanol was added to a mixture of Molecular Sieves 3A, 20 mg of 5-methyl-2-(4,4,5,5-tetramethyl-1,3,2-dioxaborolan)-2-yl)phenol, 82 mg of 1,3-dimethylpyrazole and 34 mg of copper(II) acetate dihydrate. 0.074 mL of diisopropylethylamine was further added thereto, and the resulting mixture was stirred under room temperature. When the obtained organic layer was quantitated, then 14 mg of 2-(3,5-dimethyl-1H-pyrazol-1-yl)-5-methylphenol was obtained.

Example 25: Preparation of 2-(3,5-dimethyl-1H-pyrazol-1-yl)-5-methylphenol 3 mL of 2-propanol was added to a mixture of 19 mg of 5-methyl-2-(4,4,5,5-tetramethyl-1,3,2-dioxaborolan)-2-yl)

phenol, 78 mg of 1,3-dimethylpyrazole and 32 mg of copper(II) acetate dihydrate, and the resulting mixture was stirred under room temperature. When the obtained organic layer was quantitated, then 12 mg of 2-(3,5-dimethyl-1H-pyrazol-1-yl)-5-methylphenol was obtained.

Example 26: Preparation of 2-(3,5-dimethyl-1H-pyrazol-1-yl)-5-methylphenol 3 mL of dehydrated 2-propanol was added to a mixture of 19 mg of 5-methyl-2-(4,4,5,5-tetramethyl-1,3,2-dioxaborolan)-2-yl)phenol, 78 mg of 1,3-dimethylpyrazole and 31 mg of anhydrous copper(II) acetate, and the resulting mixture was stirred under room temperature. When the obtained organic layer was quantitated, then 13 mg of 2-(3,5-dimethyl-1H-pyrazol-1-yl)-5-methylphenol was obtained.

Example 27: Preparation of 2-(3,5-dimethyl-1H-pyrazol-1-yl)-5-methylphenol 2 mL of dehydrated 2-propanol was added to a mixture of 21 mg of a crude product of (2-hydroxy-4-methylphenyl) boronic acid and 33 mg of pinacol, and the resulting mixture was stirred. To the solution were added 133 mg of 1,3-dimethylpyrazole, 50 mg of anhydrous copper(II) acetate and 1 mL of dehydrated 2-propanol, and the mixture was stirred under room temperature overnight. Insoluble materials were filtered off, the obtained organic layer was quantitated, and then 17 mg of 2-(3,5-dimethyl-1H-pyrazol-1-yl)-5-methylphenol was obtained.

Example 28: Preparation of 2-(3,5-dimethyl-1H-pyrazol-1-yl)-5-methylphenol 2 mL of tetrahydrofuran was added to a mixture of 49 mg of a crude product of (2-hydroxy-4-methylphenyl)boronic acid and 38 mg of pinacol, and the resulting mixture was stirred. To the mixture was added 38 mg of pinacol, and the mixture was further stirred overnight. To the solution were added a solution of 310 mg of 1,3-dimethylpyrazole in 3.5 mL of tetrahydrofuran, 117 mg of anhydrous copper(II) acetate and 2 mL of tetrahydrofuran, and the mixture was stirred under room temperature overnight. Insoluble materials were filtered off, the obtained organic layer was quantitated, and then 42 mg of 2-(3,5-dimethyl-1H-pyrazol-1-yl)-5-methylphenol was obtained.

Example 29: Preparation of 2-(3,5-dimethyl-1H-pyrazol-1-yl)-5-methylphenol 5 mL of tetrahydrofuran was added to a mixture of 106 mg of a crude product of (2-hydroxy-4-methylphenyl)boronic acid and 165 mg of pinacol, and the resulting mixture was stirred. To the solution were added 671 mg of 1,3-dimethylpyrazole, 5 mL of tetrahydrofuran, 117 mg of anhydrous copper(II) acetate and 10 mL of tetrahydrofuran, and the mixture was stirred at 65° C. overnight. When the obtained organic layer was quantitated, then 111 mg of 2-(3,5-dimethyl-1H-pyrazol-1-yl)-5-methylphenol was obtained.

Example 30: Preparation of 2-(3,5-dimethyl-1H-pyrazol-1-yl)-5-methylphenol 10 mL of ethyl acetate was added to a mixture of 501 mg of a crude product of (2-hydroxy-4-methylphenyl)boronic acid and 779 mg of pinacol, and the resulting mixture was stirred. The solution was subject to solvent substitution and concentration with 2-propanol. To the solution were added 20 mL of 2-propanol, 3.169 g of 1,3-dimethylpyrazole and 1.198 g of anhydrous copper(II) acetate, and the mixture was stirred at 65° C. overnight. Insoluble materials were filtered off, the obtained organic layer was quantitated, and then 440 mg of 2-(3,5-dimethyl-1H-pyrazol-1-yl)-5-methylphenol was obtained.

Example 31: Preparation of 2-(3,5-dimethyl-1H-pyrazol-1-yl)-5-methylphenol

In 4 mL of dehydrated 2-propanol were suspended 101 mg of a crude product of (2-hydroxy-4-methylphenyl)boronic acid, 71 mg of 1,3-dimethylpyrazole, 12 mg of anhydrous copper(II) acetate and 10 mg of bipyridine, 0.56 mL of diisopropylethylamine was added thereto, and the resulting mixture was stirred at 65° C. When the obtained organic layer was quantitated, then 6 mg of 2-(3,5-dimethyl-1H-pyrazol-1-yl)-5-methylphenol was obtained.

Example 32: Preparation of 2-(3,5-dimethyl-1H-pyrazol-1-yl)-5-methylphenol

In 2 mL of dimethylformamide were suspended 319 mg of 1,3-dimethylpyrazole and 121 mg of anhydrous copper (II) acetate, and the suspension was stirred at 65° C. To the suspension was added a solution of 101 mg of a crude product of (2-hydroxy-4-methylphenyl)boronic acid in 1 mL of dimethylformamide. The mixture was stirred for further 3 hours, the obtained organic layer was quantitated, and then 35 mg of 2-(3,5-dimethyl-1H-pyrazol-1-yl)-5-methylphenol was obtained.

Example 33: Preparation of 2-(3,5-dimethyl-1H-pyrazol-1-yl)-5-methylphenol

To 101 mg of (2-hydroxy-4-methylphenyl)boronic acid and 151 mg of pinacol was added 2 mL of ethyl acetate, and the mixture was stirred overnight. Ethyl acetate was evaporated off under reduced pressure, the residue was added to a mixture in which 319 mg of 1,3-dimethylpyrazole and 121 mg of anhydrous copper(II) acetate had been suspended in 2 mL of dimethylformamide, and stirred at 65° C. overnight. The resulting mixture was further stirred for 3 hours, and when the obtained organic layer quantitated, then 98 mg of 2-(3,5-dimethyl-1H-pyrazol-1-yl)-5-methylphenol was obtained.

Experimental Example: Crystal Form Stability Test

With regard to the crystals of the compounds of the formula (1), these were preserved under the following mentioned temperature and humidity conditions, and then powder X-ray diffractions were measured. As a result, in either of the measurement times, no change in crystal form was observed. According to these results, it was understood that the Form A crystals of the compounds of the formula (1) were extremely stable and high purity for a long period of 6 months or longer even under the accelerated conditions.
Test 1
Term: 12 months
Preservation condition: 25±2° C./60±5% RH*
Packaging form: Polyethylene double bag/fiber drum
Test 2
Term: 6 months
Preservation condition: 40±2° C./75±5% RH*
Packaging form: Polyethylene double bag/fiber drum
*: RH: relative humidity

TABLE 1

| | At starting | Preservation period (months) | | | | |
|---|---|---|---|---|---|---|
| | | 1 | 3 | 6 | 9 | 12 |
| Test 1 25° C./60% RH | Form A (99.7%)* | — | Form A (99.9%)* | Form A (98.9%)* | Form A (99.9%)* | Form A (99.0%)* |
| Test 2 40° C./75% RH | | Form A (100.3%)* | Form A (100.6%)* | Form A (100.4%)* | — | — |

*Content (%)

INDUSTRIAL APPLICABILITY

According to the method of the present invention, 2-(3,5-dimethyl-1H-pyrazol-1-yl)-5-methylphenol useful as an anti-trichophyton agent can be prepared as a crystalline solid without through a harmful starting material(s) or an intermediate(s). The crystals of 2-(3,5-dimethyl-1H-pyrazol-1-yl)-5-methylphenol obtained by the process of the present invention have an extremely high stability, so that they are easy and simple in preservation or handling without setting any specific preservation conditions, whereby they are extremely useful in the fields of industrial manufacturing in terms of a formulation, circulation, etc.

The invention claimed is:

1. A crystal form of a compound represented by the following formula (1):

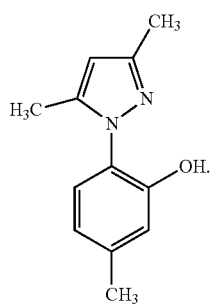

(1)

2. The crystal form according to claim 1, wherein the crystal form shows characteristic peaks at diffraction angles (2θ±0.2) of 9.3°, 16.6°, 19.2°, 21.6° and 21.9° in a powder X-ray diffraction pattern.

3. The crystal form according to claim 1, wherein the crystal form shows characteristic peaks at diffraction angles (2θ±0.2) of 9.3°, 12.7°, 16.6°, 17.3°, 17.9°, 19.2°, 21.3°, 21.6°, 21.9° and 25.7° in a powder X-ray diffraction pattern.

4. The crystal form according to claim 1, wherein the crystal form shows characteristic peaks at diffraction angles (2θ±0.2) of 9.3°, 12.7°, 16.6°, 17.3°, 17.9°, 19.2°, 21.3°, 21.6°, 21.9°, 24.0° and 25.7° in a powder X-ray diffraction pattern.

5. A process for preparing a compound represented by the following formula (1):

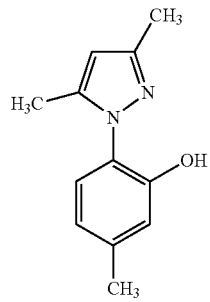

(1)

which comprises the step of reacting a compound represented by the following formula (2):

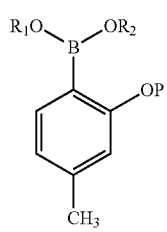

(2)

wherein $R_1$ and $R_2$ each independently represent a hydrogen or a $C_{1-6}$ alkyl, or $R_1$ and $R_2$ are combined together to form a linear or branched $C_{2-6}$ alkylene, and P represents a hydrogen atom or a protective group for a hydroxy group, with a compound represented by the following formula (3):

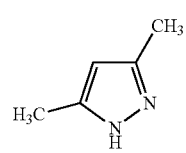

(3)

in the presence or absence of a base, and when P represents a protective group for a hydroxy group, which further comprises the step of removing the protective group P.

6. The process according to claim 5, wherein the reaction of the compound represented by the formula (2) with the compound represented by the formula (3) is carried out by using a copper reagent as a catalyst.

7. The process according to claim 5, wherein $R_1$ and $R_2$ of the compound represented by the formula (2) are combined together to form a 2,3-dimethylbutan-2,3-diyl group.

8. The process according to claim 5, wherein the reaction of the compound represented by the formula (2) with the compound represented by the formula (3) is carried out in the absence of a base.

9. A process for preparing a compound represented by the following formula (1):

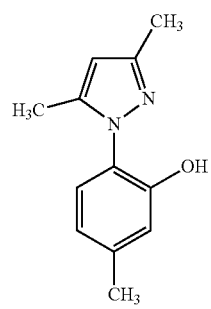
(1)

which comprises the steps of reacting a compound represented by the following formula (5):

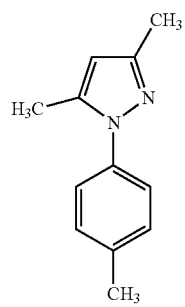
(5)

with an alkyl lithium reagent and a boric acid ester to obtain a compound represented by the formula (6):

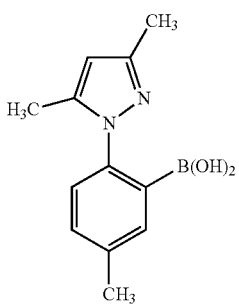
(6)

and further oxidizing the resulting compound represented by the formula (6).

10. A compound represented by the following formula (6):

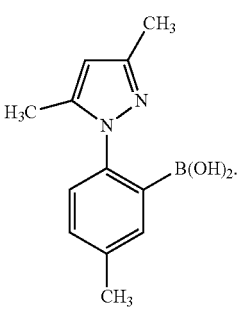
(6)

11. A pharmaceutical composition comprising the crystal form according to claim 1.

12. The process according to claim 6, wherein $R_1$ and $R_2$ of the compound represented by the formula (2) are combined together to form a 2,3-dimethylbutan-2,3-diyl group.

13. The process according to claim 6, wherein the reaction of the compound represented by the formula (2) with the compound represented by the formula (3) is carried out in the absence of a base.

14. The process according to claim 7, wherein the reaction of the compound represented by the formula (2) with the compound represented by the formula (3) is carried out in the absence of a base.

15. The process according to claim 12, wherein the reaction of the compound represented by the formula (2) with the compound represented by the formula (3) is carried out in the absence of a base.

* * * * *

UNITED STATES PATENT AND TRADEMARK OFFICE
CERTIFICATE OF CORRECTION

PATENT NO. : 10,562,858 B2
APPLICATION NO. : 15/503094
DATED : February 18, 2020
INVENTOR(S) : Sasaki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*